United States Patent
Cahan et al.

(10) Patent No.: US 11,371,071 B2
(45) Date of Patent: Jun. 28, 2022

(54) CELL CULTURING STRUCTURE INCLUDING GROWTH MEDIUM AND NON-GROWTH MEDIUM

(71) Applicant: International Business Machines Corporation, Armonk, NY (US)

(72) Inventors: Amos Cahan, Netaim (IL); Guy M. Cohen, Ossining, NY (US); Theodore G. van Kessel, Millbrook, NY (US); Sufi Zafar, Briarcliff Manor, NY (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 438 days.

(21) Appl. No.: 15/671,713

(22) Filed: Aug. 8, 2017

(65) Prior Publication Data
US 2019/0048390 A1    Feb. 14, 2019

(51) Int. Cl.
| | | |
|---|---|---|
| *C12Q 1/02* | (2006.01) | |
| *C12Q 1/18* | (2006.01) | |
| *G01N 21/59* | (2006.01) | |
| *G01N 27/04* | (2006.01) | |
| *G01N 15/06* | (2006.01) | |
| *C12M 1/12* | (2006.01) | |
| *C12M 1/34* | (2006.01) | |
| *C12M 1/00* | (2006.01) | |
| *C12M 3/00* | (2006.01) | |
| *C12M 1/18* | (2006.01) | |

(52) U.S. Cl.
CPC ............ *C12Q 1/02* (2013.01); *C12M 1/18* (2013.01); *C12M 1/3453* (2013.01); *C12M 3/00* (2013.01); *C12M 23/34* (2013.01); *C12M 25/14* (2013.01); *C12M 31/02* (2013.01); *C12M 41/36* (2013.01); *C12Q 1/18* (2013.01); *G01N 15/0656* (2013.01); *G01N 21/59* (2013.01); *G01N 27/04* (2013.01); *C12N 2533/76* (2013.01); *G01N 2201/08* (2013.01)

(58) Field of Classification Search
CPC ... C12Q 1/02; C12Q 1/04; C12Q 1/06; C12Q 2304/80; C12Q 2523/313; C12Q 1/18; G01N 15/0656; G01N 21/59; G01N 27/04; G01N 2201/08
See application file for complete search history.

(56) References Cited

U.S. PATENT DOCUMENTS

| | | | |
|---|---|---|---|
| 5,134,070 A | 7/1992 | Casnig | |
| 5,270,173 A | 12/1993 | Yonemori et al. | |
| 9,435,734 B2 | 9/2016 | Sugiyama et al. | |
| 10,309,958 B2 | 6/2019 | Sa'ar et al. | |
| 2004/0091397 A1* | 5/2004 | Picard | B01D 67/0088 422/400 |
| 2005/0019799 A1 | 1/2005 | Grasso et al. | |
| 2009/0244532 A1 | 10/2009 | Letant et al. | |
| 2010/0291575 A1 | 11/2010 | Shamah et al. | |
| 2011/0118128 A1* | 5/2011 | Garcia Tello | G01N 33/54373 506/7 |
| 2011/0218365 A1 | 9/2011 | Burns-Guydish et al. | |
| 2013/0143254 A1* | 6/2013 | Thomas | G01N 33/54373 435/29 |
| 2013/0225444 A1* | 8/2013 | Huang | C12Q 1/025 506/10 |
| 2013/0316442 A1 | 11/2013 | Meurville et al. | |
| 2014/0080729 A1 | 3/2014 | Grego et al. | |
| 2014/0378328 A1 | 12/2014 | Chakravarty et al. | |
| 2015/0118688 A1 | 4/2015 | Weidemaier et al. | |

FOREIGN PATENT DOCUMENTS

CN    101698879 A    4/2010

OTHER PUBLICATIONS

Jones, E et al. Basics of assay equipment and instrumentation for high throughput screening. Updated Apr. 2, 2016. In: Sittampalam, GS et al., editors. Assay Guidance Manual [online], [Retrieved on May 13, 2019]. Retrieved from the Internet< URL: https://www.ncbi.nlm.nih.gov/books/NBK92014/> (Year: 2016).*
List of IBM Patents or Patent Applications Treated as Related; (Appendix P), filed Nov. 6, 2019; 2 pages.
Amos Cahan et al."CELL Culturing Structure Including Growth Medium and Non-Growth Medium", U.S. Appl. No. 16/675,347, filed Nov. 6, 2019.
List of IBM Patents or Patent Applications Treated as Related; (Appendix P), Date Filed Nov. 6, 2019; 2 pages.
List of IBM Patents or Patent Applications Treated as Related; (Appendix P), Date Filed Mar. 31, 2022; 2 pages.
Amos Cahan et al."CELL Culturing Structure Including Growth Medium and Non-Growth Medium", U.S. Appl. No. 17/708,387 , Filed Mar. 30, 2022.

* cited by examiner

Primary Examiner — David W Berke-Schlessel
Assistant Examiner — Susan E. Fernandez
(74) Attorney, Agent, or Firm — Cantor Colburn LLP; Kristofer Haggerty

(57) ABSTRACT

A structure for culturing cells includes growth medium regions on a surface of the structure. Each of the growth medium regions includes a growth medium surface configured to receive and promote growth in a cell that is being cultured. The structure includes a non-growth medium. The non-growth medium includes a non-growth medium surface configured to receive the cell that is being cultured.

4 Claims, 14 Drawing Sheets

CELL CULTURING STRUCTURE INCLUDING GROWTH MEDIUM AND NON-GROWTH MEDIUM

BACKGROUND

The present invention generally relates to culturing cells. More specifically, the present invention relates to a cell culturing structures and methods that include the use of a growth medium and non-growth medium.

A single cell is the building block for human life. The genetic material of each cell in the human body—itself composed of 100 trillion cells—holds the secret to inherited diseases, such as Tay-Sachs disease, cystic fibrosis, Alzheimer's disease, and other complex diseases like heart disease. Processes for "culturing" cells have been developed for studying the behavior of cells in response to normal and induced experimental stress, free of the variations that might arise in the whole organism. The phrase "cell culture" refers to the removal of cells from an animal or plant, along with the subsequent growth of the removed cells in a favorable artificial environment such as a Petri dish. Petri dishes can be used to culture cells, such as prokaryotic, eukaryotic, and archaea cells. Prokaryotic cells include bacteria, and eukaryotic cells include fungal or human cells. Petri dishes can be provided with a layer of agar with nutrients, which serve as a growth medium. The growth medium can be inoculated or plated with a microbe-laden sample that grows into individual colonies.

SUMMARY

Embodiments of the present invention are directed to a structure for culturing cells. A non-limiting example of the structure includes growth medium regions on a surface of the structure. Each of the growth medium regions includes a growth medium surface configured to receive and promote growth in a cell that is being cultured. The structure includes a non-growth medium. The non-growth medium includes a non-growth medium surface configured to receive the cell that is being cultured.

Embodiments of the present invention are directed to a method for monitoring cultured cells. A non-limiting example of the method includes forming a structure for culturing cells. The structure includes growth medium regions on a surface of the structure. Each of the growth medium regions includes a growth medium surface configured to receive and promote growth in a cell that is being cultured. The structure includes a non-growth medium. The non-growth medium includes a non-growth medium surface configured to receive the cell that is being cultured. The structure is inoculated with a sample to be monitored. A parameter is measured at a location of the structure after inoculating the structure with the sample.

Embodiments of the present invention are directed to a method for determining an effective antibiotic concentration. A non-limiting example of the method includes forming a structure for culturing cells. The structure includes growth medium regions on a surface of the structure. Each of the growth medium regions includes a growth medium surface configured to receive and promote growth in a cell that is being cultured and different growth medium regions include differing concentrations of an antibiotic. The structure includes a non-growth medium. The non-growth medium includes a non-growth medium surface configured to receive the cell that is being cultured. The method includes recording the concentrations of the antibiotic in each of the growth medium regions inoculating the structure with a bacteria. The method includes determining which of the growth medium regions stopped growth of the bacteria. The method includes matching the growth medium regions that stopped growth of the bacteria to the concentrations of the antibiotic in the growth medium regions that stopped growth.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

Figure 1:
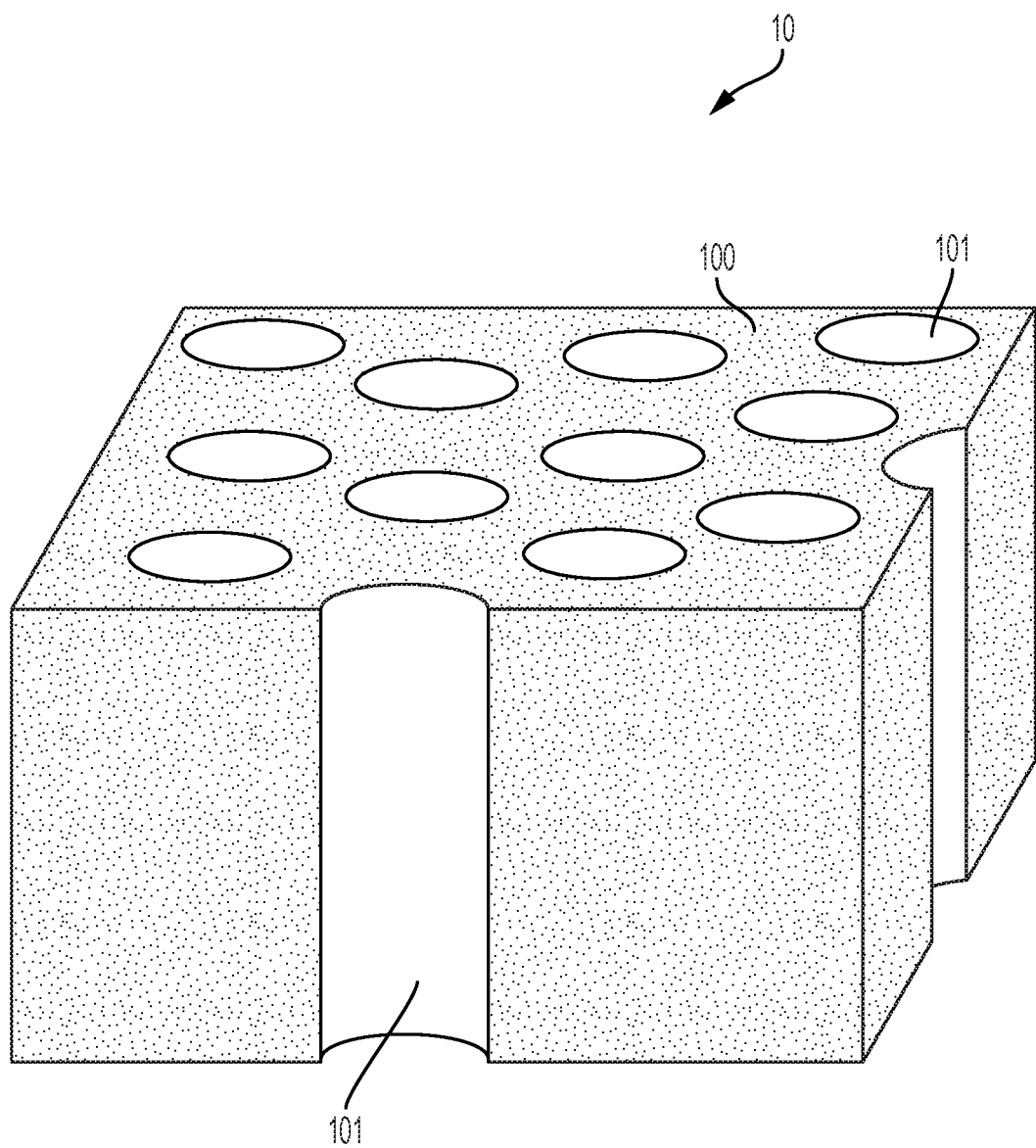
FIG. 1 depicts a perspective view of a structure for culturing cells according to one or more embodiments of the invention.

The diagrams depicted herein are illustrative. There can be many variations to the diagram or the operations described therein without departing from the spirit of the invention. For instance, the actions can be performed in a differing order or actions can be added, deleted or modified.

Also, the term "coupled" and variations thereof describes having a communications path between two elements and does not imply a direct connection between the elements with no intervening elements/connections between them. All of these variations are considered a part of the specification.

In the accompanying figures and following detailed description of the described embodiments, the various elements illustrated in the figures are provided with two or three digit reference numbers. With minor exceptions, the leftmost digit(s) of each reference number correspond to the figure in which its element is first illustrated.

DETAILED DESCRIPTION

Turning now to an overview of technologies that are more specifically relevant to aspects of the invention, as previously discussed herein, "cell culturing" involves the dispersal of cells in a favorable artificial environment composed of nutrient solutions, a suitable surface to support the growth of cells, and ideal conditions of temperature, humidity, and gaseous atmosphere. In such a system, a researcher can precisely measure the response of alterations of the cell in culture, prospective drugs, the presence or absence of other kinds of cells, carcinogenic agents, and viruses.

One example of a favorable artificial environment is a Petri dish, which can be used to culture cells such as prokaryotic, eukaryotic, and archaea cells. Prokaryotic cells include bacteria, and eukaryotic cells include fungal or human cells. The Petri dish can be provided with a growth medium (e.g., a layer of agar with nutrients), which can be inoculated or plated with a microbe-laden sample that grows into individual colonies. A growth medium such as agar can behave as a conductive medium because it contains water, ions from salts (e.g., sodium chloride (NaCl)), and nutrients such as glucose. The phrase "agar plate" is often used to describe a petri dish that contains a growth medium.

The accurate determination of cell growth and viability is pivotal to monitoring a bioprocess such as cell culturing. Cell growth in a Petri dish having an agar growth medium can be monitored by optical inspection, which can be performed with the naked eye or with the aid of an instrument such as an optical microscope. However, known methods of performing optical inspections can have a negative impact on cell cultures. For example, optical inspections require exposing the culture to light, which can be different in intensity and wavelengths than the illumination used while in storage for incubation. Some types of bacteria require light for growth but others do not. The light required for optical inspections can also affect nutrients in the agar growth medium in the Petri dish. Accordingly, the illumination required for optical inspections can skew the observed growth rate of cultures in a Petri dish.

Optical inspections, whether performed with the naked eye or by using an optical microscope, can require removal of the Petri dish lid, even if the dish lid is transparent. Removing the Petri dish lid exposes the culture to the risk of contamination. Additionally, performing optical inspection requires removing the culture from a controlled environment that provides temperature, pH, humidity, and oxygen content conditions that can be controlled and optimized for cell growth. Some microbial species must be kept in a strictly anaerobic environment because they are extremely vulnerable to oxygen. Moreover, optical inspections are done periodically and cannot provide or allow for a continuous monitoring of the growth. Finally, the spatial resolution required to identify changes in a single cell may or may not be feasible by optical inspection, even using an optical microscope, which can have a spatial resolution of a few microns.

In addition to culturing cells, agar plates (i.e., Petri dishes with growth medium) can be used to test whether bacteria are affected by antibiotics. Examples of such test include Kirby-Bauer (KB) antibiotic testing (KB testing) and disc diffusion antibiotic sensitivity testing. Wafers containing antibiotics are placed in an agar plate with bacteria, and the agar plate is left to incubate. If an antibiotic stops the bacteria from growing or kills the bacteria, there is an area around the wafer known as a zone of inhibition where the bacteria are not visible.

The zone of inhibition results from diffusion of the antibiotic in the growth medium. Diffusion leads to a concentration gradient of antibiotics, and the edge of the inhibition zone marks the minimal inhibitory concentration or the minimal antibiotic concentration that is effective in stopping the bacteria growth. Diffusion depends on various growth medium parameters such as temperature, viscosity, and the like.

Turning now to an overview of the aspects of the invention, one or more embodiments of the invention address above-described shortcomings of the prior art by providing a novel cell culturing structure and methods of using the same. In embodiments of the invention, the cell culturing structure includes a configuration of growth medium regions and non-growth medium regions. In embodiments of the invention, the growth medium regions are separated by the non-growth medium. The size and location of the growth regions and the non-growth regions of the cell culturing structure can be configured and arranged to ensure that only cells of a particular size can grow. As used herein, the phrase "non-growth medium" refers to a medium that does not provide support, e.g., nutrients, for growth of the cell.

For example, in some embodiments of the invention, the distances between adjacent growth medium regions are selected such that, in order for a cell to spread and be inoculated on the cell culturing structure, the cell must be larger than the distance between the growth medium regions. Cells having a smaller size than the distance between growth medium regions will not be able to spread to adjacent growth medium regions and will be confined to the growth medium region upon which the cells were initially deposited. The non-growth regions that are located between the growth regions do not provide support, e.g., nutrients, for growth of cells. Consequently, according to embodiments of the invention, the spacing or gap size between the growth medium regions of the novel cell structure can be chosen such that the cell structure promotes the growth of cells above a chosen size threshold.

In one or more embodiments of the invention, the novel cell culturing structure is configured to generate measurable data indicating cultured cell growth. The measurable data can be continuously detected and stored without requiring manual optical observations. In embodiments of the invention, the cell culturing structure is configured and arranged to generate the above-described measurable data by including growth medium regions separated by non-growth medium regions, along with conductive wiring or electrodes for measuring, for example, electrical impedance between the electrodes and across the cell culturing structure. The non-growth medium regions can be formed from an insulating material, and because the growth regions are separated by non-growth regions, the growth regions will not provide a conductive path between the electrodes. However, a conductive colony of conductive cells (which are undergoing a culturing process) functions as a conductive path coupling the electrodes, resulting in a lowering of the electrical impedance between the electrodes.

In embodiments of the invention, data measurement circuitry can retrieve, measure, and store the data measured from the electrodes. Accordingly, aspects of the invention address shortcomings of the prior art by providing methods for measuring data indicating cultured cell growth that reduce or eliminate the risk of culture contamination and provide or allow for a continuous monitoring of cell growth.

In some embodiments of the invention, the formation of a conductive colony of conductive cells (which are undergoing a culturing process) resulting in a lowering of a resistance between the electrodes as compared to a resistance between the electrode in the absence of the conductive colony of conductive cells that form a conductive path between the electrodes. Stated otherwise, resistance between the electrodes is relatively higher in the absence of the conductive colony of conductive cells that form a conductive path between the electrodes. Resistance between the electrodes can be continuously measured. Resistance data, and in particular a decrease in the resistance between the electrodes, can be analyzed to make determinations about how the cultured cell is growing and evolving. The cells being tracked, the growth medium regions, and the current are chosen such that the current does not skew the growth rate of the cultured cell.

In one or more embodiments of the invention, optical waveguides are placed on the cell culturing structure, light is injected in a first optical waveguide, and light intensity in or from an adjacent second optical waveguide is measured by an optical power meter. The non-growth medium can have an effective refractive index smaller than that of the material forming the optical waveguides, and because the growth regions are separated by non-growth regions, light is prevented from leaking through the cell culturing structure from one of the optical waveguides to the other through the growth regions. Thus, the cell culturing structure does not provide a path for light to be transferred between the optical waveguides. However, when a colony of cells grows so as to bridge the first optical waveguide and the adjacent second optical waveguide, a path is provided for light to be transferred between the optical waveguides through water in the cells. Accordingly, light transferred between the optical waveguides can be continuously measured and processed to track cell growth. The cells being tracked as well as the growth medium included in the cell culturing structure are chosen such that exposure to light does not skew the growth rate of the cells.

In one or more embodiments of the invention, the growth medium regions, which are separated by non-growth medium, include differing concentrations of an antibiotic. The concentration of antibiotic in each of the growth medium regions is recorded. The cell culturing structure is inoculated with a bacteria and it is determined which growth medium region(s) stopped the bacteria from growing or killed the bacteria. The bacteria as well as the growth medium regions are chosen such that optical observation does not have a negative impact on growth of the bacteria, and determining which growth medium region(s) stopped the bacteria from growing or killed the bacteria can include optical observation. Matching the growth medium region(s) that stopped the bacteria from growing or killed the bacteria to the recorded concentration of antibiotic in each of the growth medium regions provides information regarding the effective concentration(s) of the antibiotic and a minimum antibiotic concentration necessary to stop or kill the bacteria.

Above-described aspects of the invention thus address shortcomings of the prior art by allowing for determination of an accurate minimum antibiotic concentration needed to stop bacteria without relying on a diffusion model or additional measurements of the antibiotic concentration in the growth medium.

Turning now to a more detailed description of aspects of the present invention, FIG. 1 depicts a perspective view of a structure 10 for culturing cells according to embodiments of the invention. As depicted in the non-limiting embodiment shown in FIG. 1, the structure 10 includes non-growth medium 100. In some embodiments of the invention, the primary material of the structure 10 (other than the pores 101) can be formed from the non-growth medium 100. In some embodiments of the invention, the non-growth medium 100 need only be provided on an outer surface of the structure 10. The non-growth medium 100 separates the pores 101. In one or more embodiments of the invention, the non-growth medium 100 surrounds each of the pores 101 on the surface of the structure 10.

In one or more embodiments of the invention, the non-growth medium 100 is an electrically insulating material such as hafnium oxide ($HfO_2$), silicon dioxide ($SiO_2$), aluminum oxide ($Al_2O_3$), or plastic. The pores 101 and the non-growth medium 100 can extend through an entire thickness of the structure 10 and can cover the floor or bottom of a Petri dish.

The pores 101 can be formed in the non-growth medium 100 using known methods of patterning such as, for example, lithography and reactive ion etching, molding, or self-assembly methods such as those used for the formation of porous anodized alumina. The non-growth medium 100 can include anodized alumina, and the pores 101 can include a self-assembled array of pores 101 in the anodized alumina. In one or more embodiments of the invention, the non-growth medium 100 includes silicon with an oxidized surface, or surface coated with an oxide. The patterned silicon can be formed by a Bosch process. The patterned silicon can be oxidized or coated with an insulator such as an oxide or a nitride.

Figure 1A:
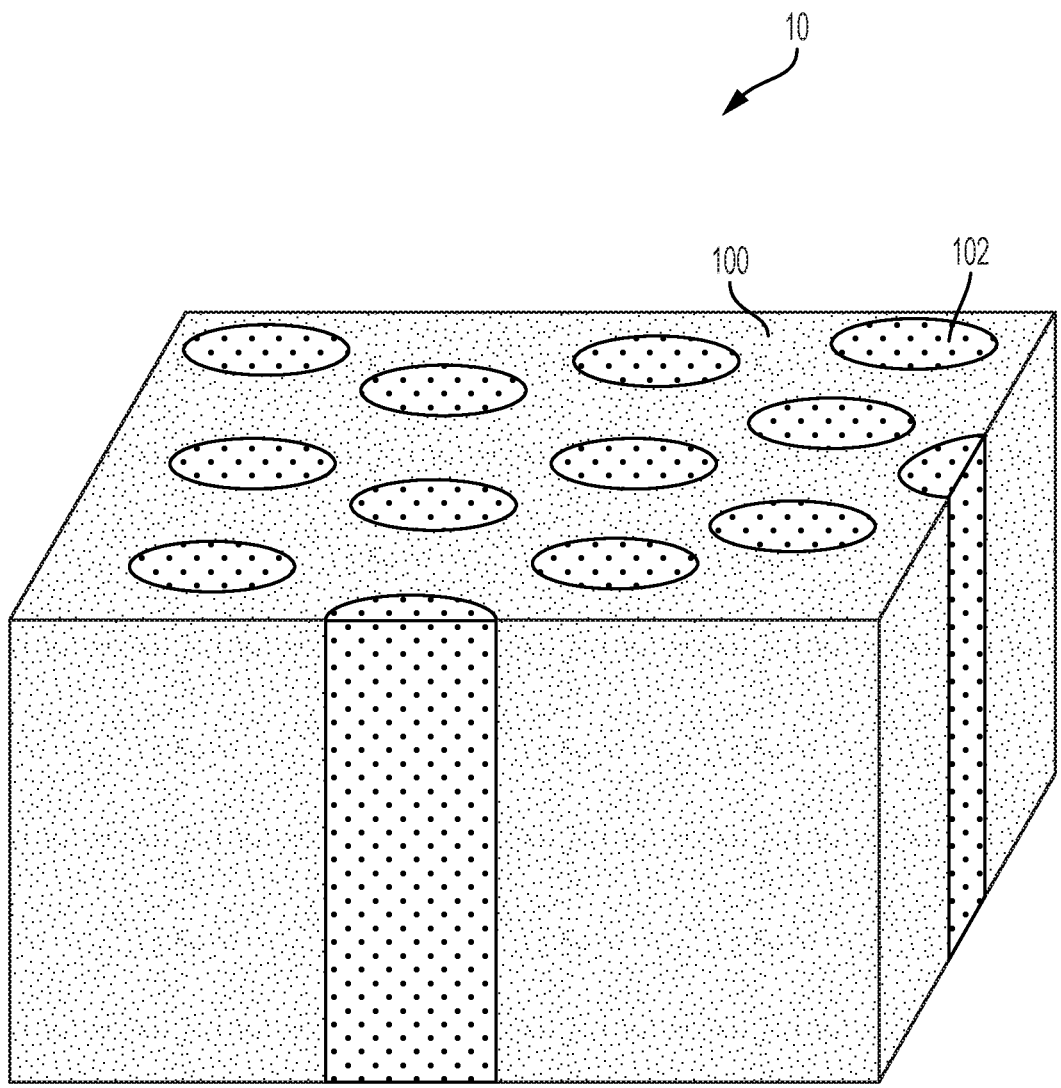
FIG. 1A depicts a perspective view of a structure for culturing cells according to one or more embodiments of the invention.

FIG. 1A depicts a perspective view of the structure 10 for culturing cells according to embodiments of the invention. As depicted in the non-limiting embodiment shown in FIG. 1A, the pores 101 are filled with growth medium, for example, agar, to form discrete growth medium regions 102. The discrete growth medium regions 102 can be in the form of, for example, pillars, cylinders, or an array thereof.

In filling the pores 101 with growth medium (to form the discrete growth medium regions 102), the growth medium can form a continuous thin film (not depicted) on a top surface of the structure 10. For example, the pores 101 can be overfilled with growth medium, which can result in excess growth medium on a top surface of the structure 10. In one or more embodiments of the invention, growth medium is removed from a surface of the structure 10 by shaving or scraping the top surface of the structure 10. In some embodiments of the invention, a top surface of the structure 10 includes or is coated with a material such that the growth medium 102 does not wet. For example, the surface material is chosen such that the contact angle of a liquid agar with the surface is larger than 90° so the agar will not wet the surface. The choice of surface materials is explained below in more detail, with reference to FIGS. 2 and 3.

According to one or more embodiments of the invention, at least one of the location, pattern, and size of the pores 101 in the structure 10 for culturing cells as depicted in the non-limiting embodiment shown in FIG. 1 can be varied. Furthermore, the structure can further include additional materials to aid in the formation of the structure 10 for culturing cells as depicted in the non-limiting embodiment shown in FIG. 1A.

Figure 2:
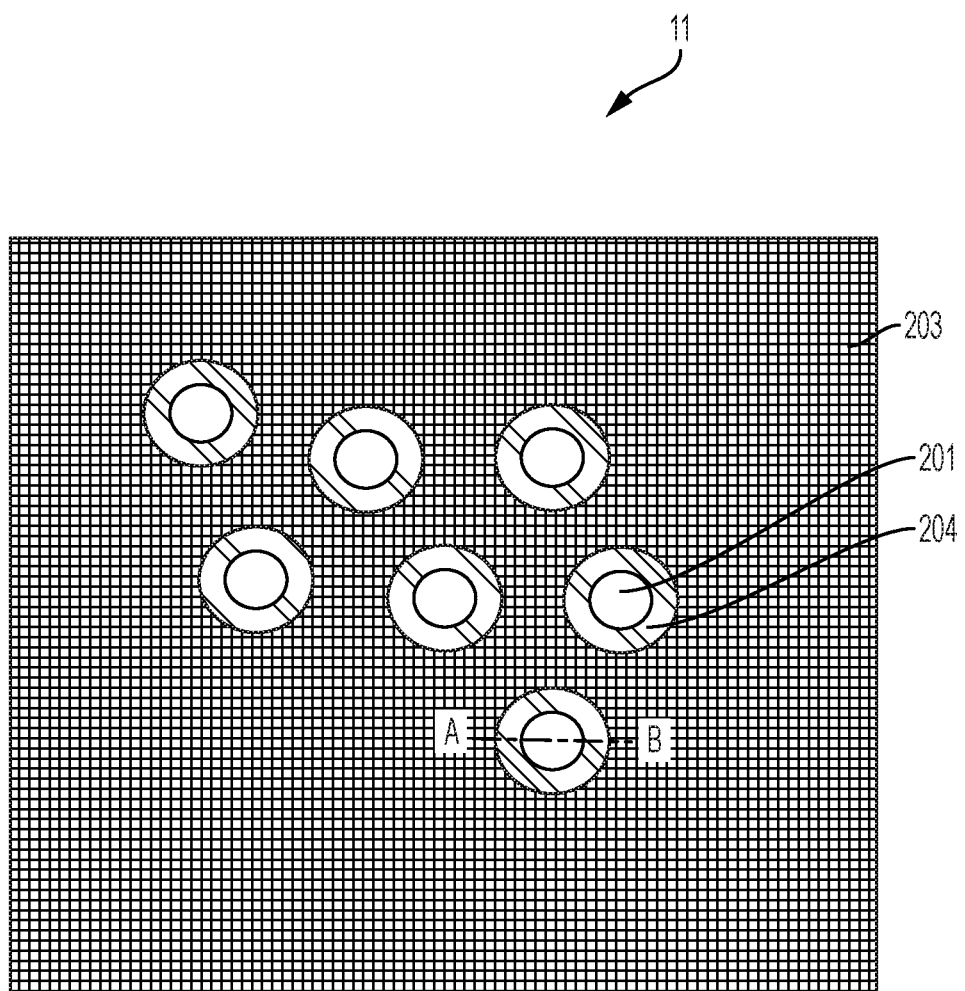
FIG. 2 depicts a top view of a structure for culturing cells according to one or more embodiments of the invention.
Figure 3:
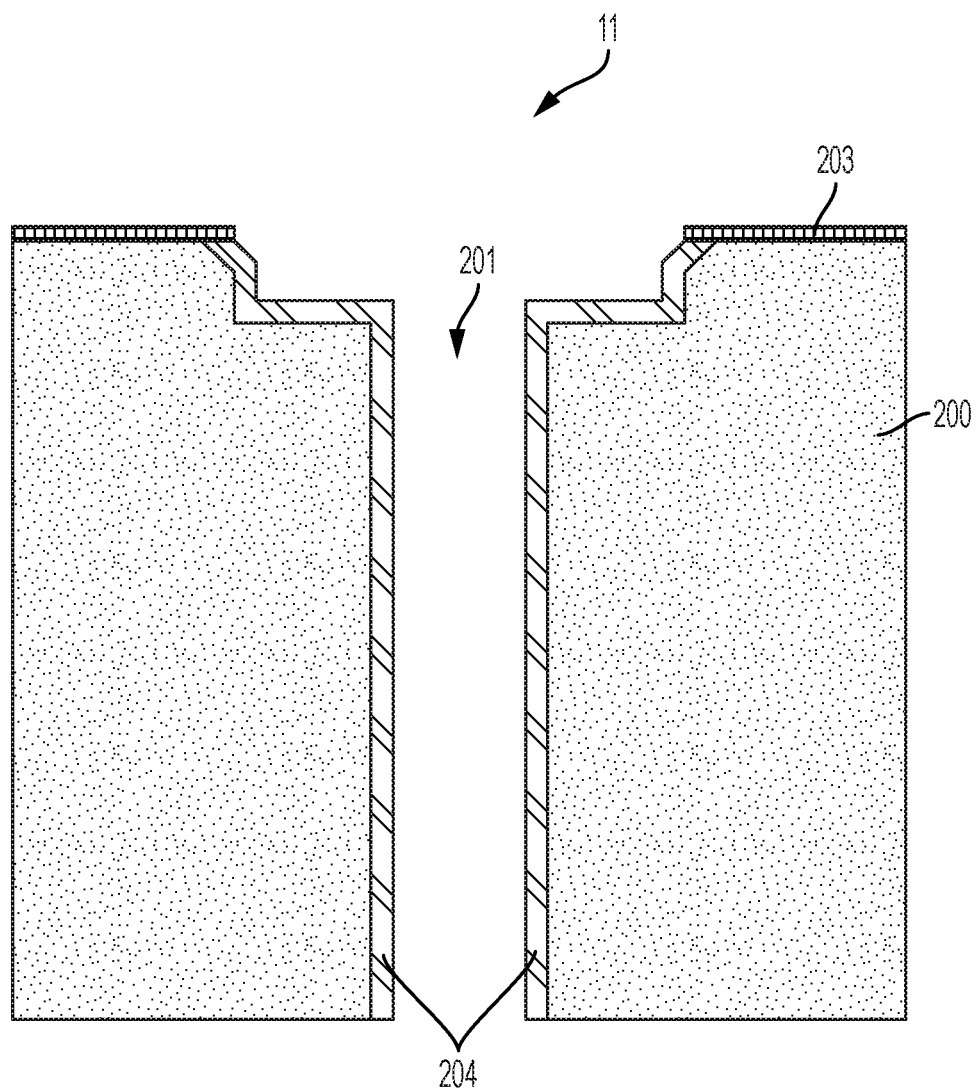
FIG. 3 depicts a cross-sectional view of the structure for culturing cells as shown in FIG. 2, along line A-B.

Thus, FIG. 2 depicts a top view of a structure 11 for culturing cells according to one or more embodiments of the invention, and FIG. 3 depicts a cross-sectional view of the structure 11 for culturing cells as shown in FIG. 2, along the line A-B. As depicted in FIGS. 2 and 3, and as best shown in FIG. 3, a hydrophobic coating 203 is formed on a top surface of the non-growth medium 200 adjacent to a groove or pore 201 in the non-growth medium 200. The pore 201 also includes a hydrophilic coating 204 formed on sidewalls of the pore 201. The hydrophilic coating 204 extends through the non-growth medium 200. The pore 201 can include an upper portion having a larger diameter than a lower portion of the pore 201. The hydrophilic coating 204 can coat sidewalls of the lower portion of the pore 201, sidewalls of the upper portion of the pore 201, and a lower surface of the upper portion of the pore 201. The hydrophobic coating 203 formed on a top surface of the non-growth medium 11 repels a growth medium (not depicted) containing water, while the hydrophilic coating 204, which attracts the growth medium containing water, draws the growth medium containing water into the pore. Thus, growth medium containing water is minimized or prevented from forming on a top surface of the structure 11.

According to one or more embodiments of the invention, at least one of the location, pattern, and size of the growth medium regions 102 in the structure 10 for culturing cells as depicted in the non-limiting embodiment shown in FIG. 1A can be varied. In some embodiments, the size and pattern of growth medium regions 102 are chosen, for example, to promote cell growth.

Figure 4:
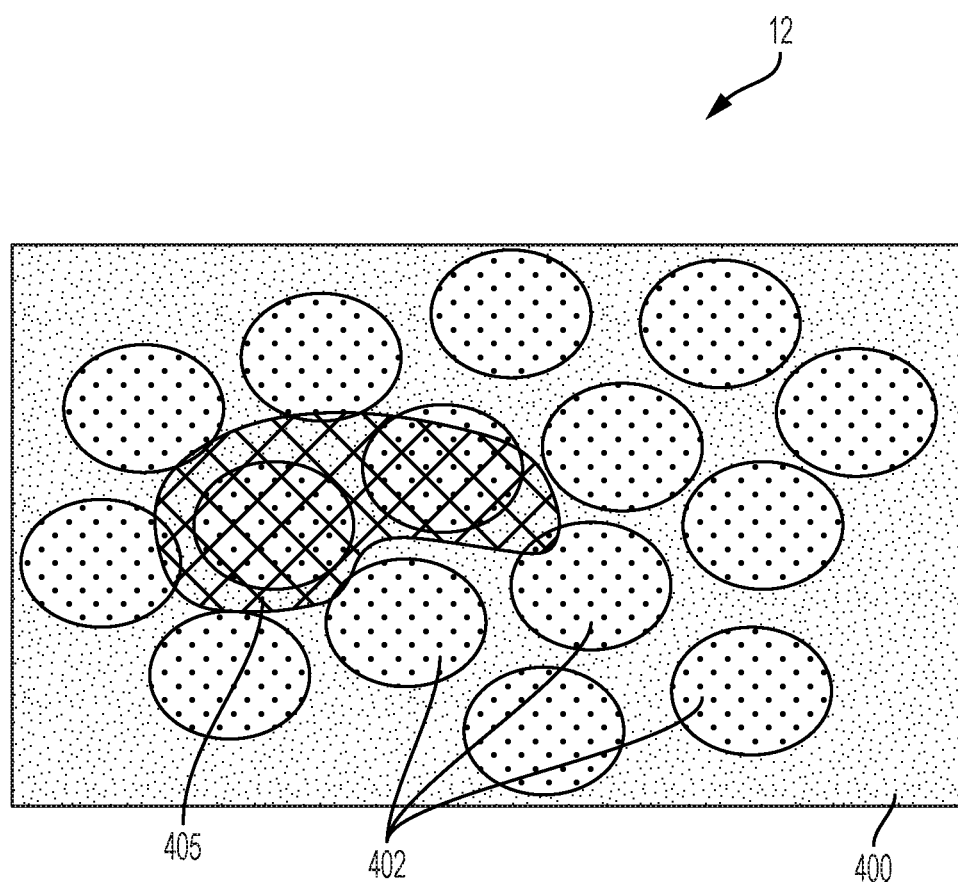
FIG. 4 depicts a top view of a structure for culturing cells according to one or more embodiments of the invention, as well as a cell.

Thus, FIG. 4 depicts a top view of the structure 12 for culturing cells as shown in FIG. 1, as well as a cell 405 dispersed onto a surface of the structure 12. As depicted in the non-limiting embodiment shown in FIG. 4, the cell 405 is overlaid on portions of the non-growth medium 400 and the discrete growth medium regions 402, and the size of the cell 405 is larger than a distance between the discrete growth medium regions 402. Accordingly, the cell 405 contacts a plurality of growth medium regions 402, which provide sufficient nutrients to support growth of the cell 405, and the culture grows. The cell can be conductive, and water content in the cell can allow for light to transfer through the cell and between adjacent cells (not depicted).

The size of a single cell 405 can be, for example, up to several micrometers, depending on cell type. In one or more embodiments of the invention, the cross-sectional area of each of the discrete growth medium regions 402 are from about 20 nm to about 200 microns or about from about 1 micron to about 18 microns. The distance between the discrete growth medium regions 402 can be in the range of from about 20 nm to about 200 nm.

Figure 5:
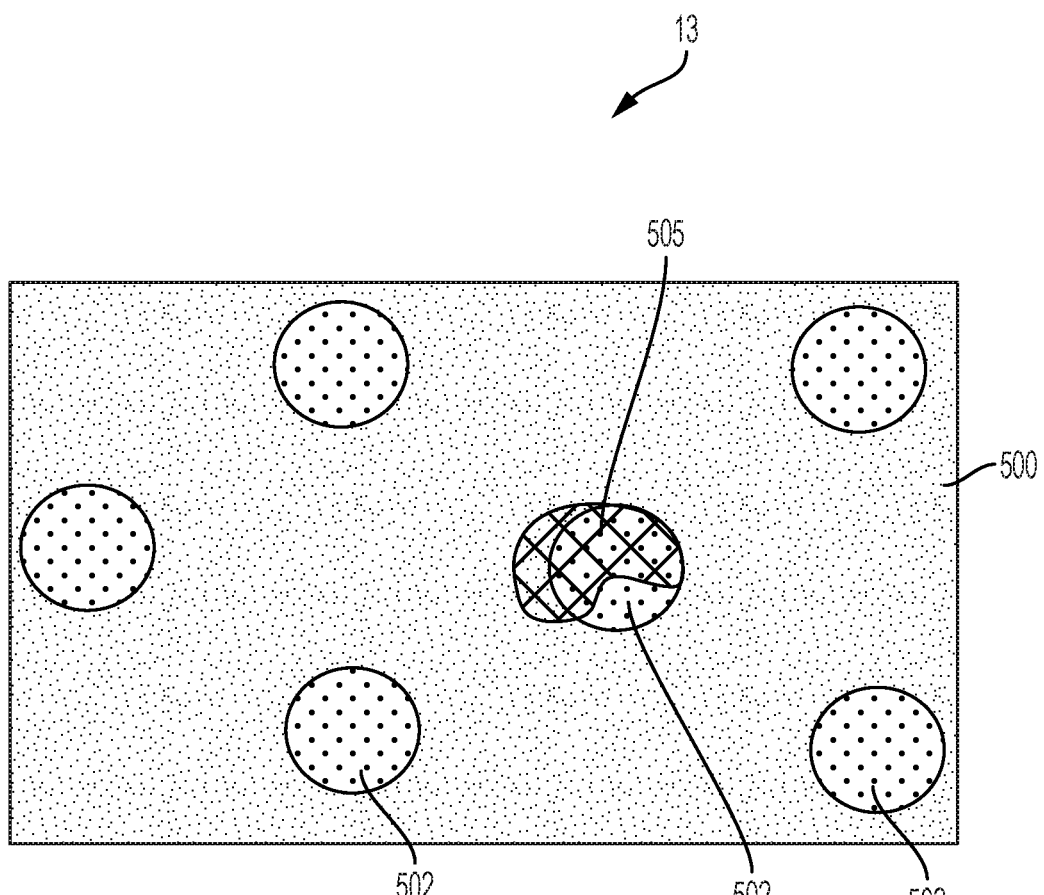
FIG. 5 depicts a top view of a structure for culturing cells according to one or more embodiments of the invention.

FIG. 5 depicts a top view of a structure 13 for culturing cells according to one or more embodiments of the invention. As depicted in the non-limiting embodiment shown in FIG. 5, the size of the cell 505 is smaller than the distance between adjacent discrete growth medium regions 502. The discrete growth medium regions 502 do not separately provide sufficient nutrients to support growth of the cell 505, and culture growth is prohibited. In other words, cells require contact with several adjacent growth regions to grow. The distance between the discrete growth medium regions 502 can be adjusted to enable only cells above a certain size threshold to grow. Cells smaller than the distance between the discrete growth medium regions 502 cannot spread to the next discrete portion of the growth medium. In this manner, the distance between the discrete growth medium regions 502 can be used to select the growth of cells above a predetermined size and prohibit the growth of smaller cells.

The structure 13 can serve as a selective medium without the need to alter other growth conditions such as growth medium or use of selective antibiotics. For example, a cellular culture of eukaryote cells contaminated by bacteria smaller than the eukaryote cells can be decontaminated using a distance between the discrete growth medium regions 502 smaller than the size of the eukaryote cells and larger than that the size of the bacteria. In one or more embodiments of the invention, the structure 13 is applied in other cell growth arrangements such as micro wells.

Provided herein are several structures that allow electrical monitoring of the culture growth. The electrical monitoring enables continuous monitoring of the culture from the early stage of the growth and can be done in-situ, which reduces or eliminates the risk of culture contamination. The continuous monitoring can be done without the need to transfer a Petri dish to a monitoring instrument, such as an optical microscope, which also reduces or eliminates the risk of culture contamination.

Figure 6:
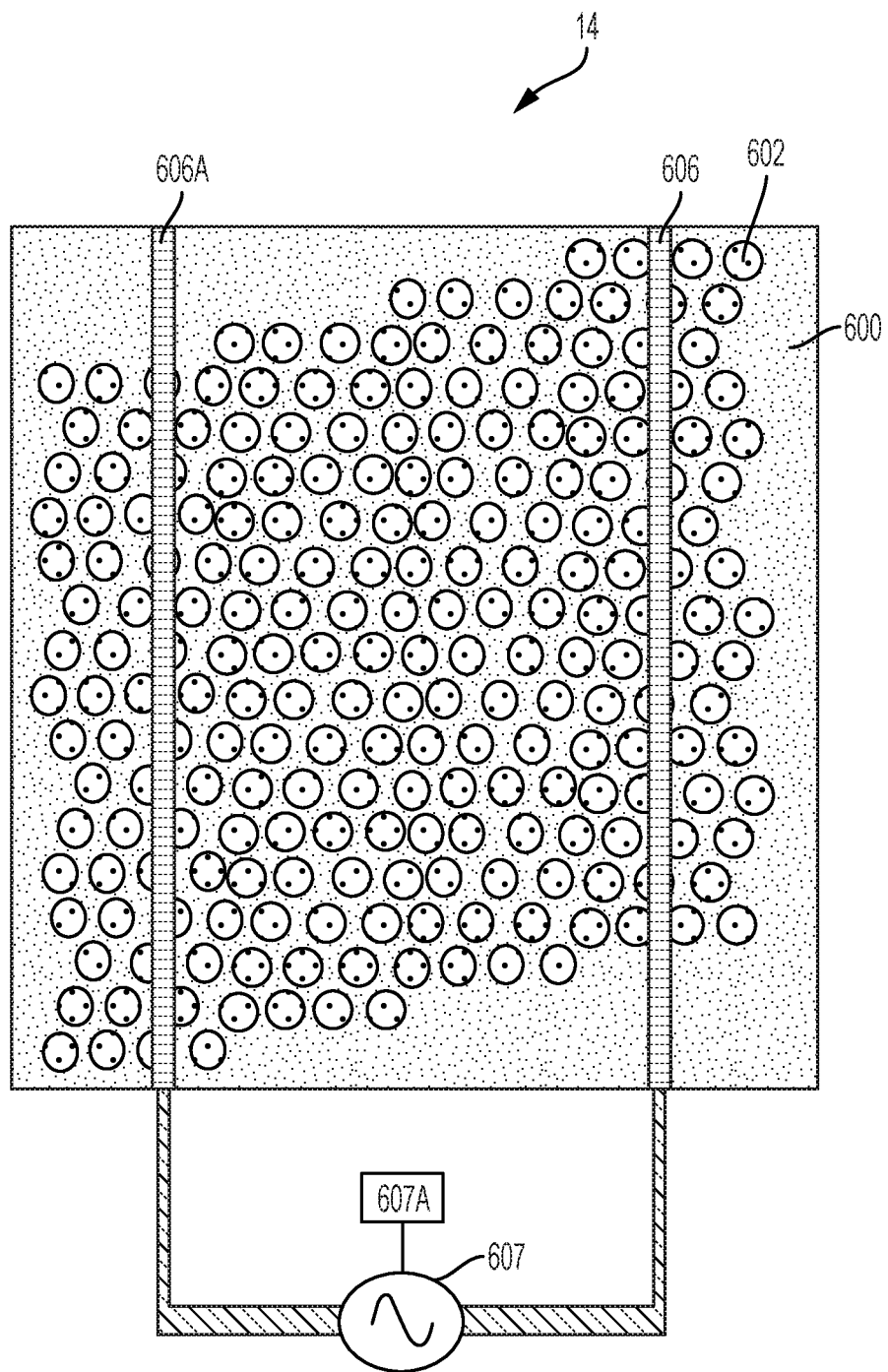
FIG. 6 depicts a top view of a structure for monitoring cultured cells according to one or more embodiments of the invention.

FIG. 6 depicts a top view of a structure 14 for monitoring cultured cells according to one or more embodiments of the invention. As depicted in the non-limiting embodiment shown in FIG. 6, a first conductive electrodes 606 and a second conductive electrode 606A are configured and arranged as shown on the structure 14, which includes non-growth medium 600 and discrete growth medium regions 602. The electrodes 606, 606A are connected to an electrical measurement device 607. The electrical measurement device 607 can be an impedance meter that can measure the impedance between the electrodes 606, 606A. In one or more embodiments of the invention, the electrodes 606, 606A include TiN. In embodiments of the invention, the non-growth medium 600 is configured to include insulating material, and the structure 14 can be a good insulator. As a result, there will not be a conductive path between the electrodes 606, 606A. A controller or processor 607A connected to the matrix chip (not depicted) or electrical measurement device, such as an Ohm meter, can continuously, continually, or periodically measure the resistance between pairs of electrodes in the array. In the example shown in FIG. 6, no cells are currently being cultured.

The culture can be inoculated onto the structure 14, for example, by streaking or printing. Lines of culture can initially be inoculated in a manner parallel to the electrodes 606, 606A. In one or more embodiments of the invention, the inoculation of the culture is automated. In one or more embodiments of the invention, the inoculation of the culture is automated using a jet printer. Alignment of the culture lines with respect to the electrodes 606, 606A can be achieved using alignment marks that can also be printed on the structure 14 when the electrodes 606, 606A are formed.

Figure 7:
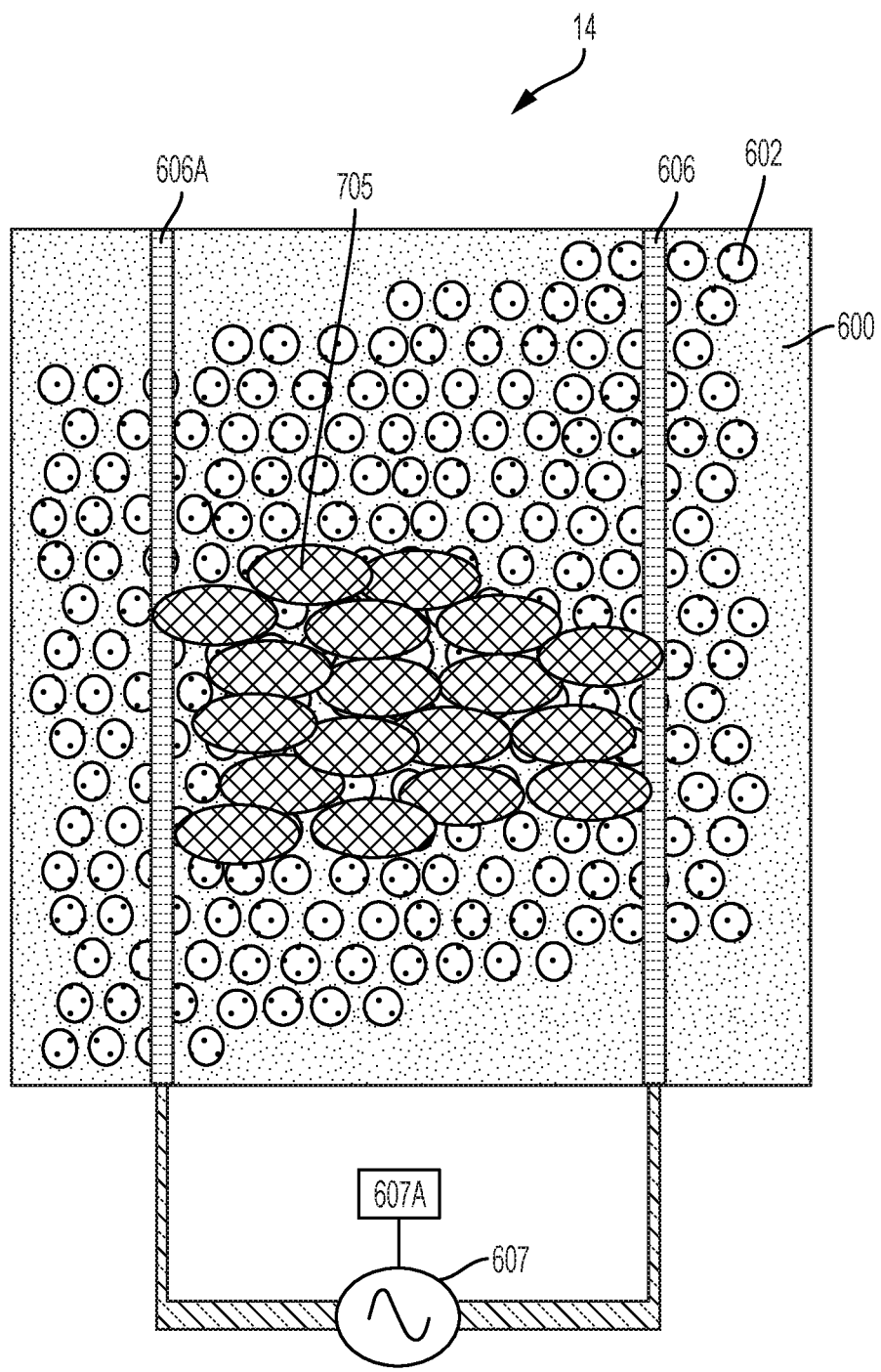
FIG. 7 depicts a top view of a structure for monitoring cultured cells according to one or more embodiments of the invention.

FIG. 7 depicts a top view of the structure 14 for monitoring cultured cells according to one or more embodiments of the invention. As depicted in the non-limiting embodiment shown in FIG. 7, the structure 14 allows for the formation of a conductive colony of conductive cells 705 that functions as a conductive path coupling electrodes 606, 606A. Consequently, the resistance between the electrodes 606, 606A is lowered. The electrodes 606, 606A are connected to an electrical measurement device 607. Resistance between the electrodes 606, 606A can be continuously measured. Resistance data can be analyzed to make determinations about how the cells 705 are growing and evolving. The cells 705, the growth medium regions 602, and the current are chosen such that the current does not skew the growth rate of the cells 705.

For ease of discussion the structure 14 is depicted as including a single pair of electrodes 606, 606A. However, the structure 14 can include any number of electrodes. In one or more embodiments of the invention, an array of parallel electrodes (not depicted) is printed or patterned on the structure 14. The distance between adjacent electrodes can vary from about one micron to hundreds of microns. The growing culture can form a colony coupling the pair of electrodes with the smallest spacing. Over time, the colony can grow bigger and can overlap electrode pairs with increasingly larger spacing.

The array of electrodes can provide a more sensitive detection of cell growth than, for example, a single pair of electrodes. A matrix chip (not depicted) can be connected to the array of electrodes to enable the selection of any pair of electrodes, and resistance between the electrodes can be measured in a similar manner as is done for a single pair of electrodes. A conductive colony including conductive cells need only couple a selected pair of electrodes to provide a change in the impedance measured between the selected pair of electrodes. The spacing of the selected pair of electrodes can be less than a spacing between other electrodes, which are not coupled by the colony.

As described above, the controller or processor 607A can continuously, continually, or periodically measure the resistance between pairs of electrodes in the array. The measured resistance between pairs of electrodes coupled by the colony is lower than the resistance of the portions of the structure 14 not coupled by the colony. The controller or processor 607A can record resistance data as a function of time. A graph of the colony size as a function of the growth time because inoculation can be generated, and the growth rate can be calculated. The processor can be included in, for example, a programmable data processing apparatus or device.

The colony growth rate can be studied as a function of cell type such as genetically modified cells, ambient conditions, medium composition, and/or use of drugs such as antibiotics. Monitoring can require only an electrical connection to one or more Petri dishes, and the monitoring of cell growth can be done continuously and in the storage place of the Petri dishes. In one or more embodiments of the invention, the electrical connection includes use of a cable or a radio-frequency identification (RFID). In this manner, monitoring can be done without a need to transfer the Petri dish to an optical microscope or to remove the lid of the Petri dish.

Figure 8:
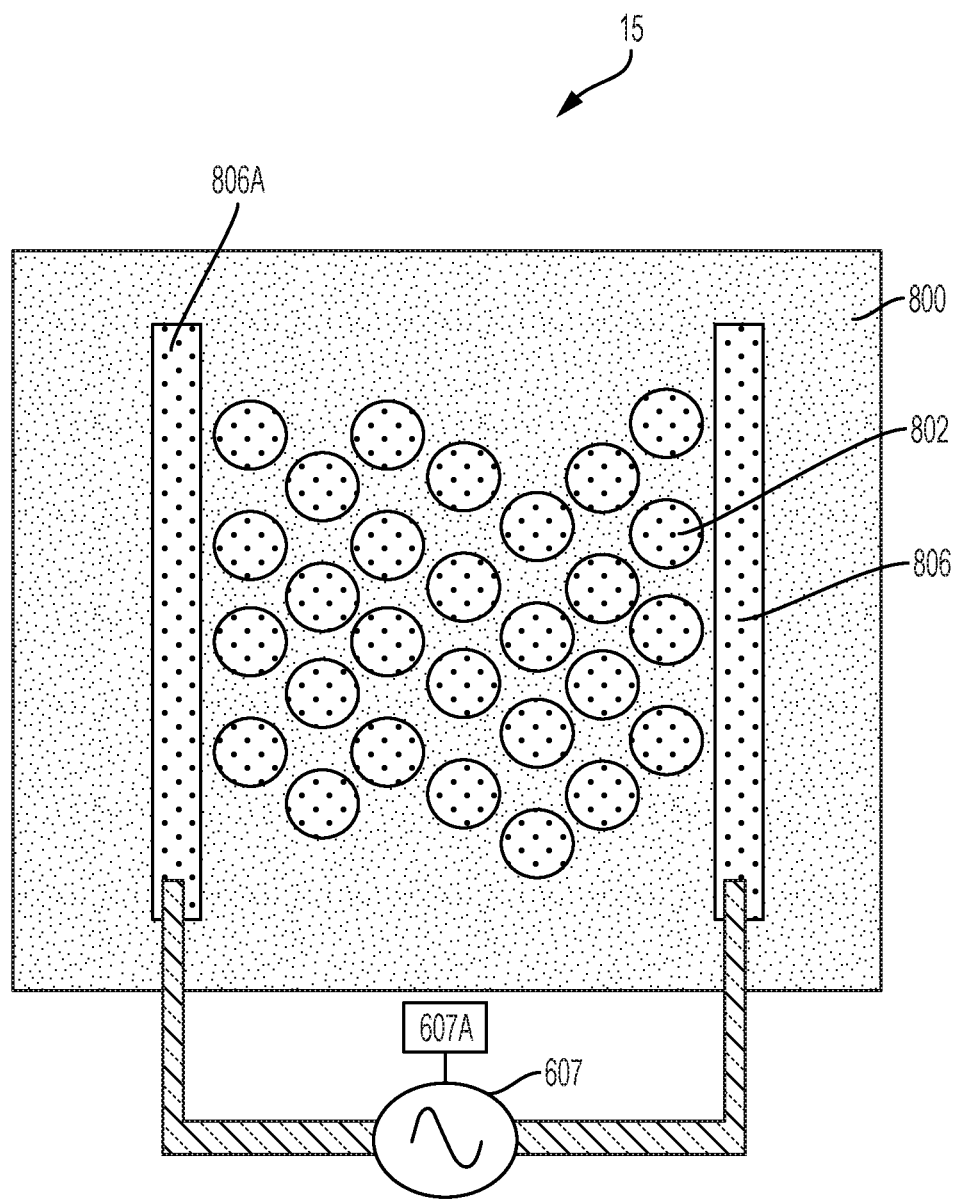
FIG. 8 depicts a top view of a structure for monitoring cultured cells according to one or more embodiments of the invention.

FIG. 8 depicts a top view of a structure 15 for monitoring cultured cells according to one or more embodiments of the invention. As depicted in the non-limiting embodiment shown in FIG. 8, non-growth medium 800 and discrete growth medium regions 802 are located between growth medium regions 806, 806A in the form of trenches. The growth medium regions 806, 806A are connected to an electrical measurement device 607, which can measure the impedance between the growth medium regions 806, 806A. When a culture including conductive cells forms a conductive colony (not depicted) coupling the growth medium regions 806, 806A, the impedance changes. This change in impedance is measured over time according to one or more embodiments of the invention. The growth medium regions 806, 806A replace the electrodes that are present the embodiment depicted in FIGS. 6-7. Accordingly, electrodes are not necessary and cost savings and/or ease in forming the structure 15 can be realized. In the example shown in FIG. 8, no cells are currently being cultured.

Figure 9:
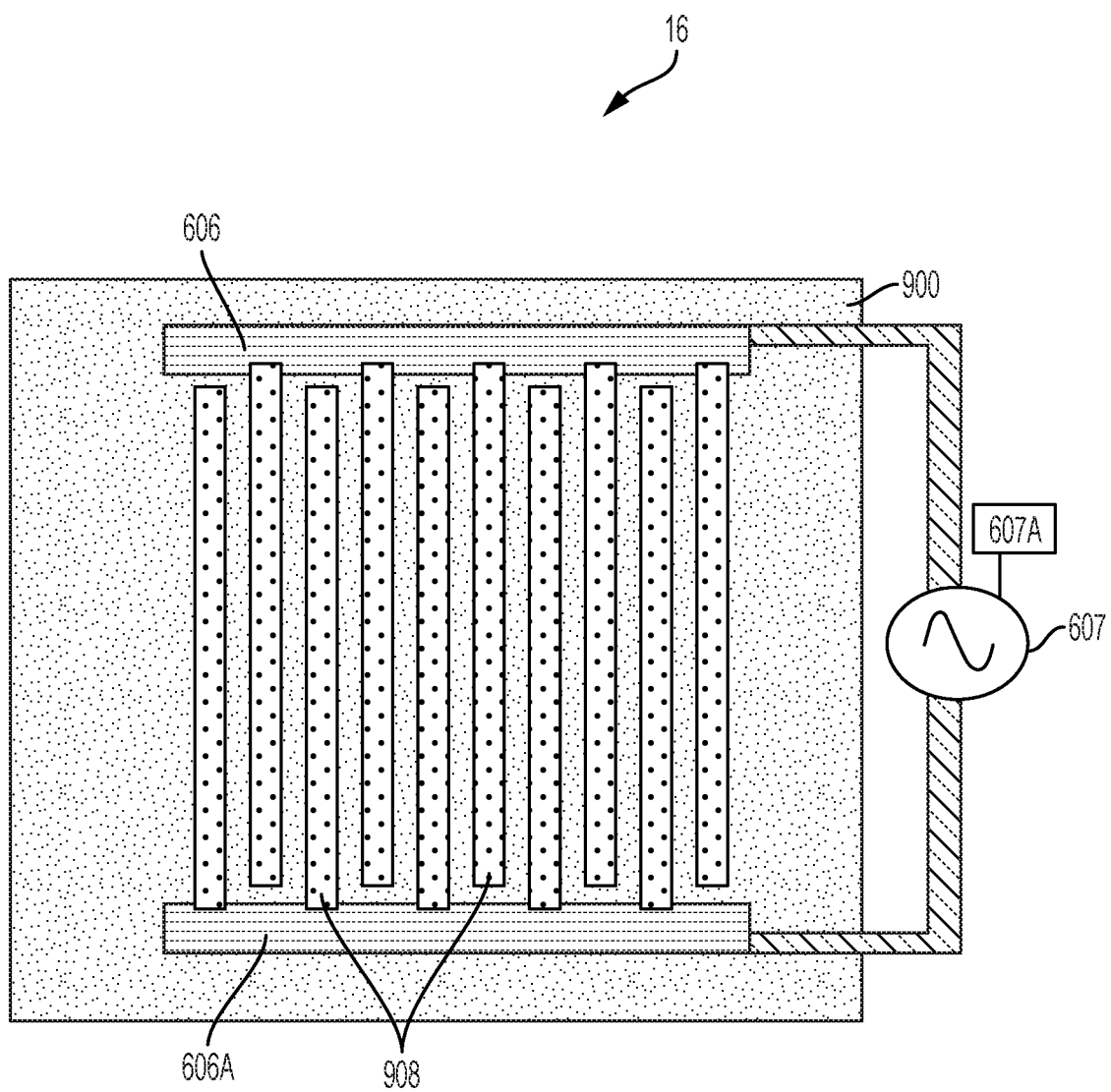
FIG. 9 depicts a top view of a structure for monitoring cultured cells according to one or more embodiments of the invention.

FIG. 9 depicts a top view of a structure 16 for monitoring cultured cells according to one or more embodiments of the invention. As depicted in the non-limiting embodiment shown in FIG. 9, discrete growth medium regions 908 in the form of interdigitated trenches are each connected to an electrode 606, 606A and are separated by non-growth medium 900. The electrodes 606, 606A are connected to an electrical measurement device 607, which can measure the impedance between the electrodes 606, 606A. As described above, each of the discrete growth medium regions 908 is each connected to an electrode 606, 606A, and adjacent discrete growth medium regions 908 are connected to different electrodes.

The structure 16 can provide a more sensitive detection of cell growth than, for example, the embodiment depicted in FIGS. 6-7. A conductive colony (not depicted) including conductive cells need only couple adjacent discrete growth medium regions 908, which are connected to different electrodes, rather than coupling the electrodes 606, 606A, to provide a change in the impedance measured between the electrodes 606, 606A. For example, the electrodes can be spaced farther apart then adjacent discrete growth medium regions 908. Moreover, further growth of the colony (not depicted) to couple more than two discrete growth medium regions 908 can resultantly provide greater coupling between the electrodes 606, 606A. Further change in the impedance measured between the electrodes 606, 606A can therefore indicate further growth of the colony (not depicted). Additionally, cost savings can be realized by forming the discrete growth medium regions 908, as opposed to the discrete growth medium regions 602 depicted in FIGS. 6-7. In the example shown in FIG. 9, no cells are currently being cultured.

Figure 10:
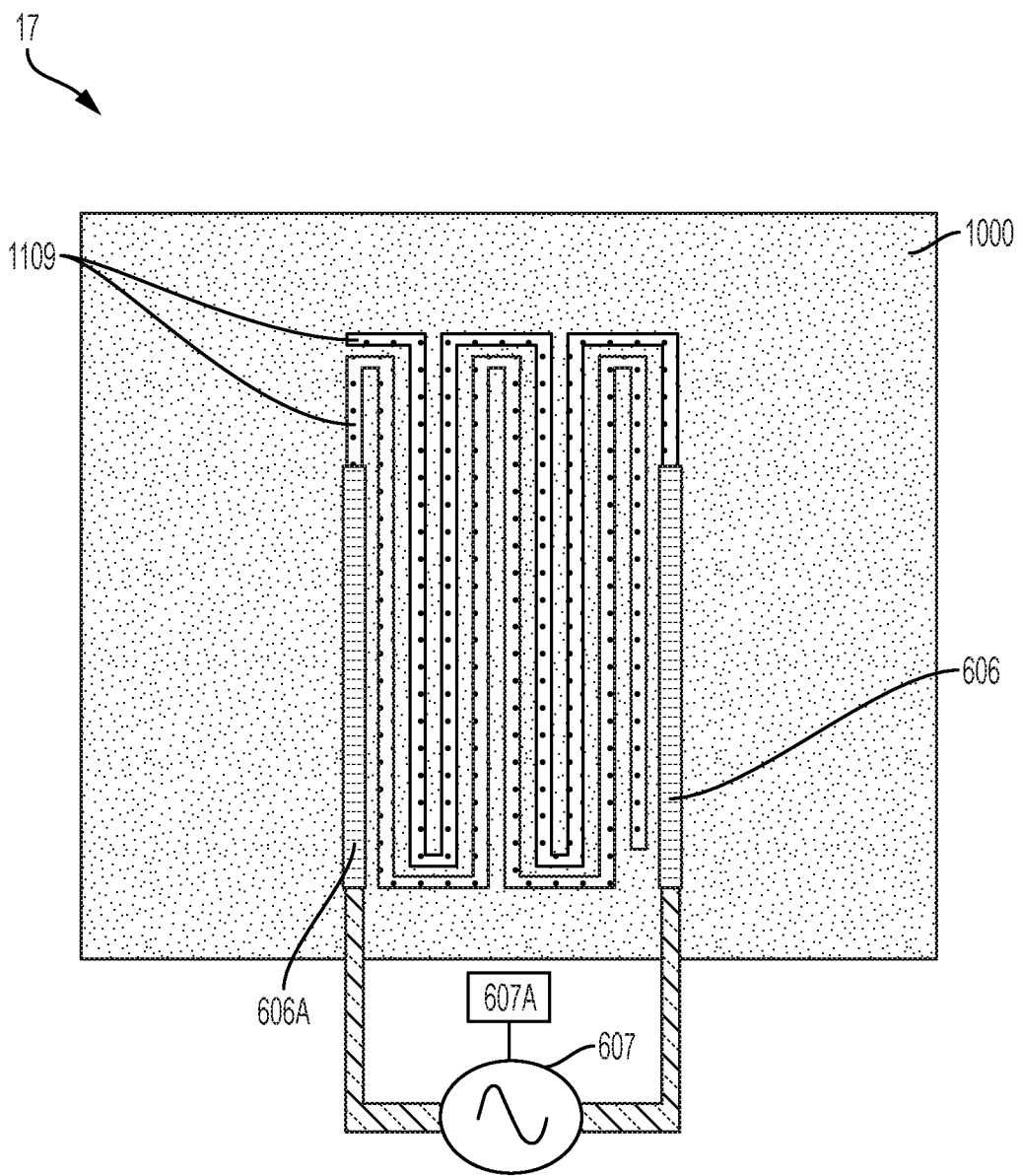
FIG. 10 depicts a top view of a structure for monitoring cultured cells according to one or more embodiments of the invention.

FIG. 10 depicts a top view of a structure 17 for monitoring cultured cells according to one or more embodiments of the invention. As depicted in the non-limiting embodiment shown in FIG. 10, discrete growth medium regions 1109 in the form of double serpentine trenches are each connected to an electrode 606, 606A and are separated by non-growth medium 1000. The electrodes 606, 606A are connected to an electrical measurement device 607, which can measure the impedance between the electrodes 606, 606A. As described above, each of the discrete growth medium regions 1109 is each connected to an electrode 606, 606A, and adjacent discrete growth medium regions 1109 are connected to different electrodes.

The structure 17 can provide a more sensitive detection of cell growth than, for example, the embodiment depicted in FIGS. 6-7. Conductive cells (not depicted) need only couple adjacent discrete growth medium regions 1109, which are connected to different electrodes, rather than coupling the electrodes 606, 606A, to provide a change in the impedance measured between the electrodes 606, 606A. For example, the electrodes can be spaced farther apart then adjacent discrete growth medium regions 1109. Moreover, further growth of the colony (not depicted) to couple additional portions of the discrete growth medium regions 1109 can resultantly provide greater coupling between the electrodes 606, 606A. Further change in the impedance measured between the electrodes 606, 606A can therefore indicate further growth of the colony (not depicted). Additionally, a smaller number of the discrete growth medium regions 1109 can be needed as compared to the discrete growth medium regions 1109 depicted in FIG. 10, and less connections to the electrodes 606, 606A can be needed. Accordingly, cost savings and/or ease in forming the structure 17 can be realized. In the example shown in FIG. 10, no cells are currently being cultured.

Figure 11:
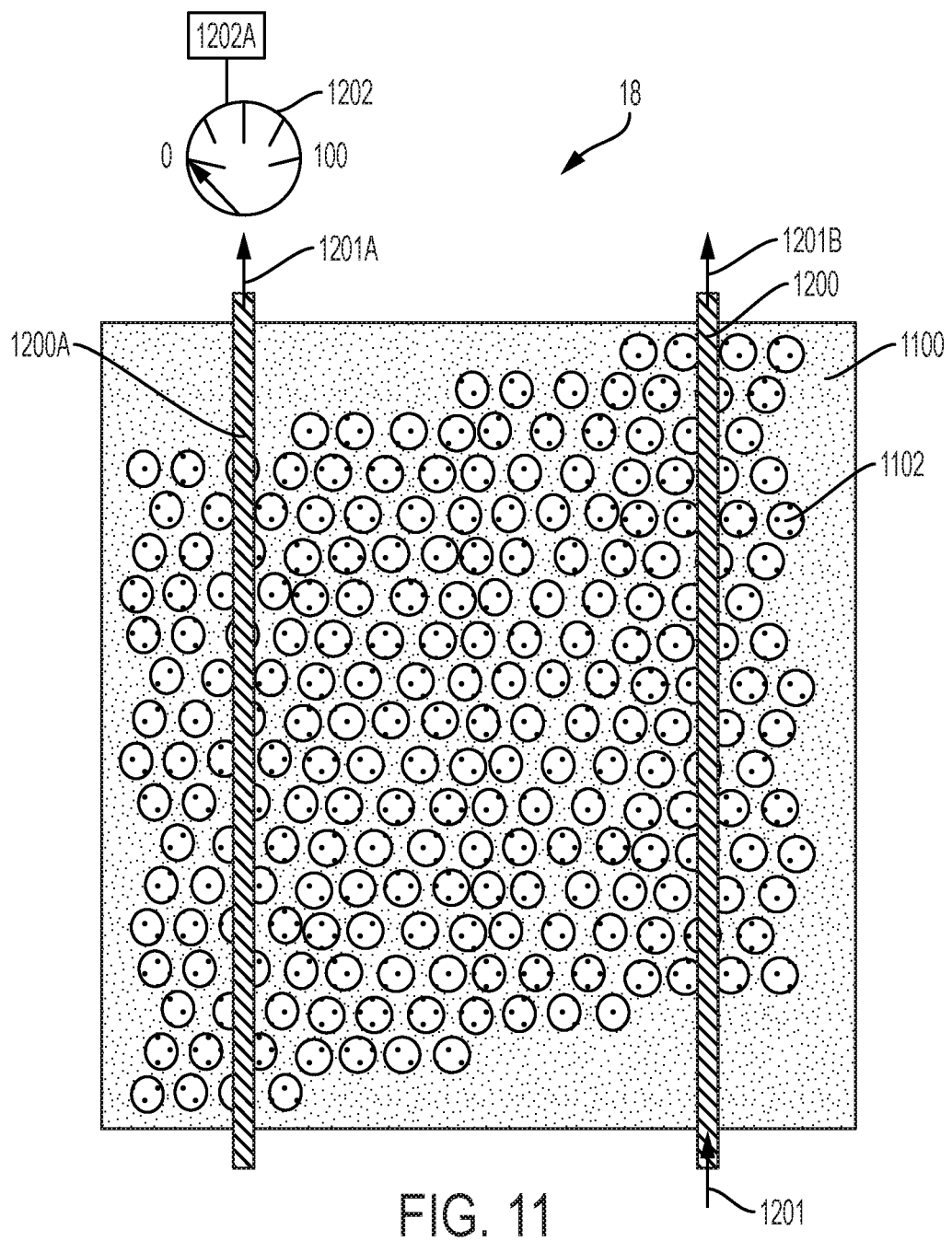
FIG. 11 depicts a top view of a structure for monitoring cultured cells according to one or more embodiments of the invention.

FIG. 11 depicts a top view of a structure 18 for monitoring cultured cells according to one or more embodiments of the invention. As depicted in the non-limiting embodiment shown in FIG. 11, a first optical waveguide 1200 and a second optical waveguide 1200A, which are substantially parallel to each other, are configured and arranged as shown on the structure 18, which includes non-growth medium 100 and discrete growth medium regions 1102. The optical waveguides 1200, 1200A can be formed using materials such as a polymer, plastic, or glass. In one or more embodiments of the invention, the polymer is a silicone resin. For ease of discussion, the structure 18 is depicted as including a single pair of waveguides 1200, 1200A. However, the structure 18 can include any number of optical waveguides.

In embodiments of the invention, portions of the structure 18 are configured to have effective refractive indices that are smaller than that of the material forming the optical waveguides. As a result, light cannot leak from one of the first optical waveguide 1200 to the second optical waveguide 1200A. The low refractive index can be achieved by making the non-growth medium 1100 between the discrete growth medium regions 1102 porous. In one or more embodiments of the invention, a low refractive index is obtained by inserting air gaps or pockets in the non-growth medium 1100 between the discrete growth medium regions 1102. In one or more embodiments of the invention, the refractive index of the non-growth medium 1100 between the discrete growth medium regions 1102 approaches that of air (i.e., the refractive index n can be about 1).

To monitor the culture growth, a light source (not depicted) is connected to the first waveguide 1200 to inject light 1201 therein, and the amount of light 1201A emitted from the second waveguide is measured. Light 1201 is injected in the first waveguide 1200 and the intensity of light (if any) that passes from the first waveguide 1200 to the second waveguide 1200A is measured by, for example, an optical power meter 1202. In the example shown in FIG. 11, no cells are currently being cultured and no light is passed from the first waveguide 1200 to the second waveguide 1200A. In the absence of an active cell culturing activity, there are not cells to optically couple the first and second waveguides 1200, 1200A. Accordingly, in the example shown in FIG. 11, the first and second waveguides 1200, 1200A are optically de-coupled, and little or none of light 1201 is leaked or transferred between the first and second waveguides 1200, 1200A. Because little or no light leaks or is transferred between the first and second waveguides 1200, 1200A, the light 1201A emitted from the second waveguide 1200A and detected by the optical power meter 1202 is substantially zero, and substantially all of the light 1201 (depending on transmission losses and length of the first waveguide 1200) that enters the first waveguide 1200 would exit as light 1201B.

Figure 12:
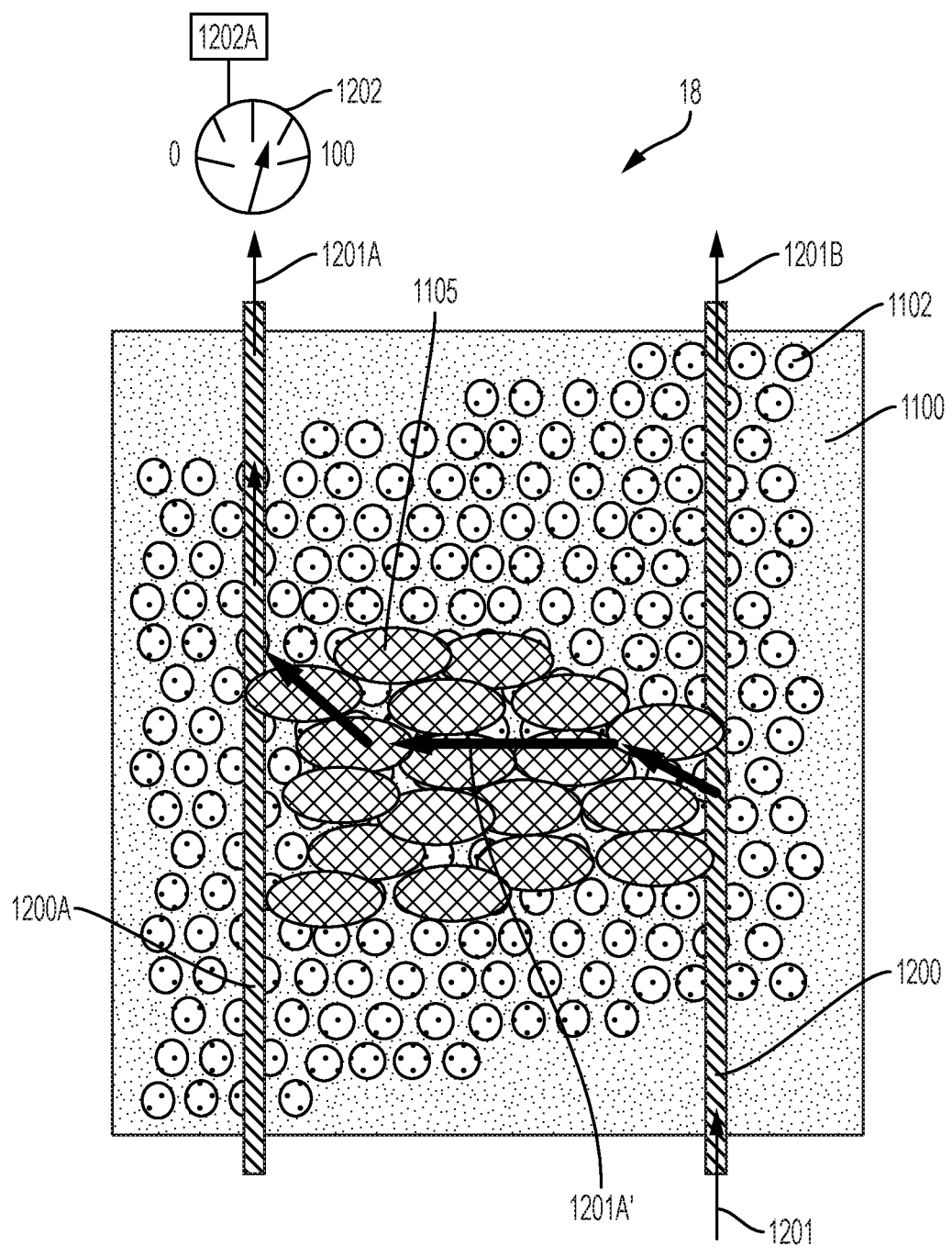
FIG. 12 depicts a top view of a structure for monitoring cultured cells according to one or more embodiments of the invention.

FIG. 12 depicts a top view of the structure 18 for monitoring cultured cells according to one or more embodiments of the invention. As depicted in the non-limiting embodiment shown in FIG. 12, cells 1105 are actively being cultured using the structure 18. The cells 1105 provide a path for optically coupling light 1201A', which is a portion of the light 1201 that enters the first waveguide 1200, to the second waveguide 1200A. Light 1201A' is transferred between the first and second waveguides (with transmission losses from traveling through a portion of the first waveguide 1200, the cells 1105 and the second waveguide 1200A) and is detected as light 1200A by the optical power meter 1202. The cells 1105 couple the first and second waveguides 1200, 1200A due to, for example, the water content of the cells 1105, which allows for light to transfer through cells, between adjacent cells, and from the first waveguide 1200 to the second waveguide 1200A. Light intensity in or from the optical waveguide adjacent to the optical waveguide in which light is injected can be continuously measured by the optical power meter 1202. Optical power data can be analyzed to make determinations about how the cultured cell is growing and evolving, thus avoiding the shortcomings described herein associated with tracking cultured cell growth and evolution through optical observations. The cells 1105 as well as the growth medium 1102 are chosen such that exposure to the light 1201 does not skew the growth rate of the cells 1105.

A controller or processor 1202A connected to the optical power meter 1202 can continuously, continually, or periodically measure the light intensity in or from the first and second optical waveguides 1200, 1200A. The controller or processor 1202A can record light intensity data as a function of time. A graph of the size of the cells 1105 as a function of the growth time because inoculation can be generated, and the growth rate can be calculated. The processor can be included in, for example, a programmable data processing apparatus or device.

Figure 13:
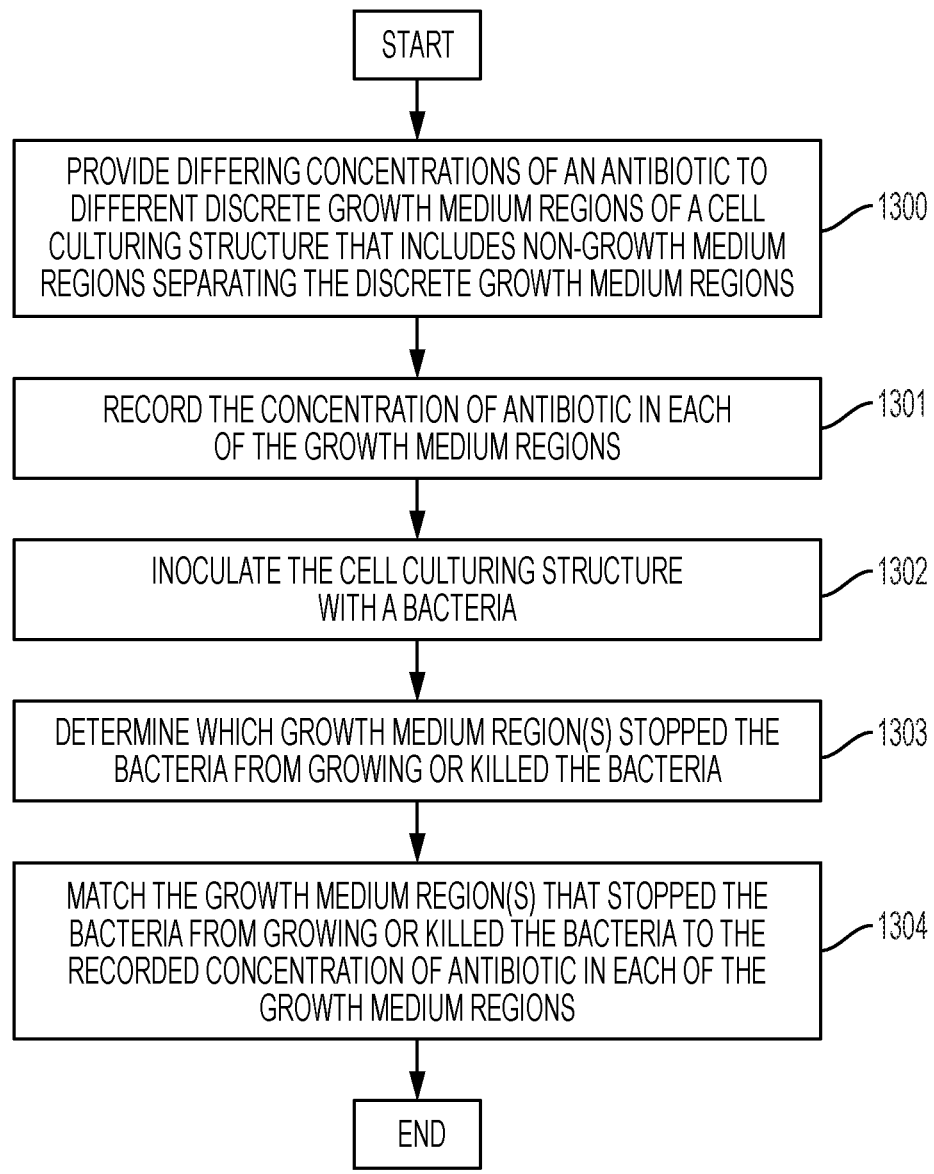
FIG. 13 depicts a flow diagram illustrating a methodology according to one or more embodiments of the present invention.

FIG. 13 depicts a block/flow diagram of an exemplary method for determining an effective antibiotic concentration according to embodiments of the invention. At block 1300, differing concentrations of an antibiotic are provided to different discrete growth medium regions of a cell culturing structure. The cell culturing structure includes non-growth medium regions separating the discrete growth medium regions. At block 1301, the concentration of antibiotic in each of the growth medium regions is recorded. At block 1302, the cell culturing structure is inoculated with a bacteria. At block 1303, it is determined which growth medium region(s) stopped the bacteria from growing or killed the bacteria. The bacteria as well as the growth medium regions are chosen such that optical observation does not have a negative impact on growth of the bacteria. Determining which growth medium region(s) stopped the bacteria from growing or killed the bacteria can include optical observation. At block 1304, the growth medium region(s) that stopped the bacteria from growing or killed the bacteria is matched to the recorded concentration of antibiotic in each of the growth medium regions. The matching provides information regarding what concentration(s) of the antibiotic stops growth of or kills the bacteria including a minimum antibiotic concentration to stop or kill the bacteria. An accurate minimum antibiotic concentration needed to stop bacteria can be determined without relying on a diffusion model or additional measurements of the antibiotic concentration in the growth medium.

More than one embodiment of the invention can be combined. For example, in one or more embodiments of the invention, an array of parallel electrodes is provided on a cell culturing structure, which includes non-growth medium regions separating the discrete growth medium regions. The electrodes are connected to an electrical measurement device, which can measure the impedance between any of the electrodes. A matrix chip can be connected to the array of electrodes to enable the selection of any pair of electrodes. Differing concentrations of an antibiotic are provided to different discrete growth medium regions of the cell culturing structure. The concentration of antibiotic in each of the growth medium regions is recorded. The cell culturing structure is inoculated with a bacteria. Growth medium regions including an effective antibiotic concentrations will kill the bacteria. Impedance between a selected pair of electrodes is measured. Different pairs of electrodes have different growth medium regions therebetween and different concentrations of antibiotic therebetween. The concentration of antibiotic between each pair of electrodes is recorded.

An impedance measured between a selected pair of electrodes will increase when the bacteria are killed by the antibiotic in the growth medium regions therebetween and the selected pair of electrodes is no longer coupled by the bacteria. Whether the bacteria is killed by an antibiotic concentration can be determined by comparing impedance measured between the selected pair of electrodes and another pair of electrodes and/or comparing impedance measured between the selected pair of electrodes and a reference measurement between the selected pair of electrodes taken immediately after inoculation of the bacteria. Moreover, matching the selected pair of electrodes with increased impedance measured therebetween to the concentration of antibiotic therebetween can provide information regarding what concentration(s) of the antibiotic kill the bacteria including a minimum antibiotic concentration to kill the bacteria. In this manner, determining which growth medium region(s) killed the bacteria can avoid optical observation.

Various embodiments of the present invention are described herein with reference to the related drawings. Alternative embodiments can be devised without departing from the scope of this invention. Although various connections and positional relationships (e.g., over, below, adjacent, etc.) are set forth between elements in the following description and in the drawings, persons skilled in the art will recognize that many of the positional relationships described herein are orientation-independent when the described functionality is maintained even though the orientation is changed. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. As an example of an indirect positional relationship, references in the present description to forming layer "A" over layer "B" include situations in which one or more intermediate layers (e.g., layer "C") is between layer "A" and layer "B" as long as the relevant characteristics and functionalities of layer "A" and layer "B" are not substantially changed by the intermediate layer(s).

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection."

References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper," "lower," "right," "left," "vertical," "horizontal," "top," "bottom," and derivatives thereof shall relate to the described structures and methods, as oriented in the drawing figures. The terms "overlying," "atop," "on top," "positioned on" or "positioned atop" mean that a first element, such as a first structure, is present on a second element, such as a second structure, wherein intervening elements such as an interface structure can be present between the first element and the second element. The term "direct contact" means that a first element, such as a first structure, and a second element, such as a second structure, are connected without any intermediary conducting, insulating or semiconductor layers at the interface of the two elements.

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate possible implementations of fabrication and/or operation methods according to various embodiments of the present invention. Various functions/operations of the method are represented in the flow diagram by blocks. In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A method for monitoring cultured cells, the method comprising:
   forming a structure for culturing cells, the structure including:
      growth medium regions formed in a plurality of pores on a surface of the structure, wherein each of the growth medium regions includes a growth medium surface configured to receive and promote growth in a cell that is being cultured; and
      a non-growth medium comprising the plurality of pores, wherein sidewalls of the pores are coated with a hydrophilic coating, and wherein a topmost surface of the non-growth medium is coated with a hydrophobic coating;
   positioning a first optical waveguide at a first location on a surface of the structure;
   positioning a second optical waveguide at a second location on a surface of the structure, the second optical waveguide not being directly connected to the first optical waveguide;
   inoculating the structure with a sample to be monitored;
   injecting light into the second optical waveguide;
   passing the light from the second optical waveguide through cells of the sample to the first optical waveguide; and
   measuring an amount of light emitted from the first optical waveguide.

2. The method of claim 1, further comprising:
   measuring an amount of the light at the first location on the structure before inoculating the structure with the sample; and comparing the amount of light measured at the first location after inoculating the structure with the sample with the amount of light measured at the first location before inoculating the structure with the sample.

3. The method of claim 1, wherein the non-growth medium separates the growth medium regions. optical waveguide.

4. The method of claim 1, wherein:

the first optical waveguide and the second optical waveguide each comprises an optical waveguide material; and the non-growth medium has a refractive index that is less than that of the optical waveguide material.

* * * * *